United States Patent [19]

Shimamune et al.

[11] Patent Number: 4,965,088

[45] Date of Patent: Oct. 23, 1990

[54] CALCIUM PHOSPHATE-COATED COMPOSITE MATERIAL AND PROCESS FOR PRODUCTION THEREOF

[75] Inventors: Takayuki Shimamune, Tokyo; Masashi Hosonuma, Kanagawa, both of Japan

[73] Assignee: Permelec Electrode Ltd., Kanagawa, Japan

[21] Appl. No.: 331,327

[22] Filed: Mar. 31, 1989

Related U.S. Application Data

[62] Division of Ser. No. 109,887, Oct. 19, 1987, Pat. No. 4,847,163.

[30] Foreign Application Priority Data

Oct. 17, 1986 [JP] Japan ................. 61-247160

[51] Int. Cl.$^5$ ............................................. A61F 1/24
[52] U.S. Cl. ............................................. 427/2; 623/16
[58] Field of Search ........................... 623/16; 427/2

[56] References Cited

U.S. PATENT DOCUMENTS

| | | | |
|---|---|---|---|
| 4,801,300 | 1/1989 | Kurze | 623/16 |
| 4,842,604 | 6/1989 | Dorman | 623/16 |
| 4,846,837 | 7/1989 | Kurze | 623/16 |

*Primary Examiner*—Sam Silverberg
*Attorney, Agent, or Firm*—Sughrue, Mion, Zinn, Macpeak & Seas

[57] ABSTRACT

A calcium phosphate-coated composite material is disclosed, comprising a metallic substrate, an oxide layer on the metallic substrate, said oxide layer consisting essentially of the oxide of one or more metals selected from the group consisting of titanium, zirconium, hafnium, niobium, tantalum, tin, cobalt, aluminum, chromium, molybdenum and tungsten, and a coating layer of calcium phosphate provided on the oxide layer. A process for production of the calcium phosphate-coated composite material is also disclosed.

8 Claims, No Drawings

CALCIUM PHOSPHATE-COATED COMPOSITE MATERIAL AND PROCESS FOR PRODUCTION THEREOF

This is a division of application Ser. No. 07/109,887, filed Oct. 19, 1987 now U.S. Pat. No. 4,847,163.

FIELD OF THE INVENTION

The present invention relates to a composite material comprising a metallic substrate coated with calcium phosphate which is excellent in affinity to the tissue of bone or teeth, which is thus useful as an implant material such as artificial bone, teeth and teeth roots, or as a bonding material for such implant materials, and a process for production thereof.

BACKGROUND OF THE INVENTION

A living body implant material such as artificial bone and an artificial tooth root has been receiving great attention in recent years because when the bone is broken and lost by an accident, for example, or the tooth is taken out, it can be restored by bonding the implant material or planting the implant material in the jaw bone, and thus the bone or tooth can be used in the nearly original form and a comforable life can be enjoyed. Since, however, the implant material is embedded in the living body, it is essential that the material be harmless to the human body and it must satisfy such requirements as sufficiently high strength, good processability, no dissolution, suitable specific density and good affinity to the living body.

Metals such as noble metals, alloys such as stainless steel, ceramics such as α-alumina, and in addition, apatite have heretofore been used as an implant material. These materials, however, have at least one of such disadvantages as toxicity is exhibited, the strength is insufficiently low, the processability is poor, dissolution occurs, and affinity to the living body is poor.

In order to eliminate the above disadvantages, it has been desired to develop metals or ceramics which when coated on the surface with apatite, provide a composite material having good affinity to the living body. For this purpose, a technique to bond metal and ceramic, or to bond ceramic and ceramic is needed. As such a metal-ceramic bonding technique or ceramic-ceramic bonding technique, only a plasma spray coating method has been known. Further this plasma spray coating method has disadvantages in that the yield of expensive apatite particles is low and the bonding between the coating and the substrate is not always sufficiently high. Moreover, if the plasma spray coating method is applied under too severe conditions, partial decomposition occurs during the spray coating process and it becomes necessary to conduct additional treatments such as crystallization.

In order to overcome the above prior art problems, the present inventors with another has proposed an implant material in which a metallic substrate and a coating of calcium phosphate are firmly bonded with an intermediate layer containing calcium phosphate sandwiched therebetween (Japanese Patent Application Nos. 64012/86, 64013/86 and 70504/86 (corresponding to U.S. patent application Ser. No. 29,519 filed Mar. 24, 1987)), and an implant material in which a metallic substrate and a coating of calcium phosphate are bonded together with no intermediate layer sandwiched therebetween (Japanese Patent Application No. 169547/86 (corresponding to U.S. patent application Ser. No. 74837 filed Jul. 17,1987)), and moreover all can be produced without the use of the spray coating method.

In these implant materials, the bonding strength between the metallic substrate and the coating of calcium phosphate is sufficiently high. However, when they are embedded in the living body, the coating of calcium phosphate having good affinity to the bone tissue may assimilate with the bone tissue, finally bringing the metallic substrate in direct contact with the bone tissue. Since the affinity of the metallic substrate to the bone tissue is poor, the bone tissue regresses, thereby degrading the bonding between the bone tissue and the metallic substrate, and in the worst case, the implant material may be rejected.

SUMMARY OF THE INVENTION

The object of the present invention is to provide a composite material which is good in workability, is of sufficiently high mechanical strength, has increased affinity to the bone tissue, and can maintain stable bonding properties over a long time, and thus which is suitable as an implant material such as an artificial bone and an artificial tooth root, and also a process for production of the composite material.

The present invention relates to a calcium phosphate-coated composite material comprising a metallic substrate, an oxide layer on the metallic substrate, the oxide layer consisting essentially of an oxide of one or more metals selected from the group consisting of titanium, zirconium, hafnium, vanadium, niobium, tantalum, tin, cobalt, aluminum, chromium, molybdenum and tungsten, and a coating of calcium phosphate provided on the oxide layer.

The present invention also relates to a process for producing a calcium phosphate-coated composite material which comprises coating a coating solution containing one or more metals selected from the group consisting of titanium, zirconium, hafnium, vanadium, niobium, tantalum, tin, cobalt, aluminum, chromium, molybdenum and tungsten on the surface of a metallic substrate, heating the resulting coating in an oxidizing atmosphere to convert the metal into the corresponding oxide and to form a layer consisting essentially of the oxide, and then forming a coating of calcium phosphate on the surface of the oxide layer.

The major feature of the present invention resides in the fact that the oxide layer of metal oxide having relatively good affinity to the living body and sufficiently high corrosion resistance is sandwiched between the metallic substrate and the coating of calcium phosphate, so that even when the coating of calcium phosphate surface layer is absorbed in the bone tissue, direct contact between the metallic substrate and the bone tissue can be prevented and thus degradation of the bonding properties between the metallic substrate and the bone tissue can be prevented.

DETAILED DESCRIPTION OF THE INVENTION

The present invention will hereinafter be explained in detail.

The present invention provides a calcium phosphate-coated composite material comprising a metallic substrate, an oxide layer on the metallic substrate, said oxide layer consisting essentially of the oxide of metals such as titanium, having excellent corrosion resistance in the living body and exhibiting good adhesion properties to the metallic substrate, and a coating of calcium phosphate on the oxide layer, which is suitable as an implant material, and a process for producing the calcium phosphate-coated composite material. In accordance with the present invention, there can be provide a composite material which can be bonded to a bone, for example, with sufficiently high affinity in the living body and moreover exhibit stable bonding properties over a long time.

The metallic substrate as used herein means a substrate made of metals such as titanium, titanium alloys and stainless steel which are stable in the living body. The titanium and titanium alloys include metallic titanium and titanium alloys of titanium and Ta, Nb, platinum group metals, Al, V and so on. The stainless steel as used herein includes, as well as so-called stainless steel such as JIS (Japanese Industrial Standards) SUS 304, 310 and 316, corrosion resistant alloys such as a cobalt-chromium alloy for implanting into the living body. The metallic substrate made of the metal as described above may be in the form of e.g., a plate and a bar, may be smooth on the surface, may have a porous surface like a sponge, or may be an expanded mesh or a porous plate. The reason why the metals as described above are used as the substrate is that the metals have a sufficiently high mechanical strength and can be easily molded in comparison with sintered materials and glass.

The surface of the metallic substrate may be previously subjected to a rinsing treatment such as washing with water, acid, supersonic waves, steam and so on, to remove impurities thereon and to increase the affinity to the oxide layer as described hereinafter. If desired, the surface of the metallic substrate may be made coarse by applying a blast and/or etching treatment to increase the affinity to the oxide layer and at the same time, to conduct activation. The above etching includes, as well as chemical etching, physical etching such as sputtering.

On the above-described metallic substrate, the oxide layer of metal oxide is formed. The oxide layer consists essentially of the oxide of one or more metals selected from the group consisting of titanium, zirconium, hafnium, vanadium, niobium, tantalum, tin, cobalt, aluminum, chromium, molybdenum and tungsten. Examples of such metal oxides are $TiO_2$, $ZrO_2$, $HfO_2$, $VO_2$, $V_2O_5$, $Nb_2O_5$, $NbO_2$, $TaO_2$, $Ta_2O_5$, $Cr_2O_3$, $Mo_2O$, $MoO_3$, $WO_3$, $SnO_2$, $Co_2O_3$, $Co_3O_4$, $CoO$, $Al_2O_3$ and their mixtures or solid solutions. In addition, the oxide layer may contain oxides in the so-called suboxide state resulting from removal of part of the oxygen in the oxide, composite oxides resulting from dissolution of the metallic substrate component, composite oxides with the calcium phosphate coating as the upper layer, and moreover undecomposed or half-decomposed products of the components in the coating solution.

The oxides of titanium, zirconium, hafnium, niobium, tantalum, tin, chromium, molybdenum and tugsten as obtained by the thermal decomposition method as described hereinafter are excellent in corrosion resistance, particularly acid resistance, and thus can be used independently. However the stability of the solution containing the salts of the above metals as described hereinafter is poor. This poor stability can be improved by adding elements having a valence number different from that of the component element. For example, an alcohol solution of tungsten chloride having a valence of 6 is easily hydrolyzed by moisture in the air and its color changes from light yellow to black purple. This color change can be considerably inhibited by adding a small amount of tantalum alkoxide having a valence of 5. An alcohol solution of titanium alkoxide having a valence of 4 is easily hydrolyzed by moisture in the air and becomes turbid or forms white precipitates. The alcohol solution can be maintained in a stable condition for a long time by adding a small amount of vanadium alkoxide having a valence of 5.

In the lower layer of the oxide layer subjected to thermal decomposition in an oxidizing atmosphere, an oxide coating of the substrate component or a layer of a mixture or solid solution of the oxide of the substrate component with the metal oxide of the oxide layer is formed. If the oxide layer subjected to thermal decomposition contains the same component as in the oxide layer of the substrate component, a completely continuous mixed oxide or solid solution layer can be formed. For example, if chromium is added to the coating solution, when stainless steel is used as the substrate, an oxide layer which is continuous in chromium density to the chromium oxide surface layer can be formed and thus a more increased bonding strength can be obtained. In the case of an Fe-Cr-Al alloy, since an alumina coating is formed on the surface, it is sufficient to add alminum to the coating. Also in the case of a Co-Cr alloy, it suffices that cobalt or chromium is added.

To form the oxide layer on the metallic substrate, it suffices that a solution containing the metal salt is coated on the metallic substrate, dried and then calcined by heating in an oxidizing atmosphere to convert the metal salt into the corresponding oxide and at the same time, to firmly bond it to the surface of the metallic substrate. In a case where the metallic substrate is made titanium or a titanium alloy, a hydrochloric acid aqueous solution or alcohol solution of e.g., the chloride or alkoxymetal salt of the above metal is used as the coating solution, which is coated on the surface of the metallic substrate which has been activated by applying pretreatment, dried and then heated in an oxidizing atmosphere, for example, at 300° to 700° C. for 5 to 30 minutes, whereupon there can be obtained a metal oxide layer firmly bonded to the metallic substrate. The reason why the above hydrochloric acid aqueous solution or alcohol solution is preferably used as the coating solution is that they corrode titanium to some extent at high temperatures and form fine irregularities in the surface of the metallic substrate, thereby further improving the bonding properties between the metallic substrate and the oxide layer.

The oxidizing atmosphere as used herein means an atmosphere containing a sufficient amount of oxygen to convert the metal into the corresponding metal oxide. It is usually sufficient to use air as the oxidizing atmosphere. Preferably, heating is carried out in a muffle furnace.

In the case where the metallic substrate is made of an anti-corrosive alloy such a stainless steel, if the coating solution contains halogen ions or a halogen compound, when the coating solution is coated and calcined, part of the halogen remains in the coating in the form of oxychloride or free halogen and, as a result, the problem of corrosion of the metallic substrate which is not encountered in the case of titanium or titanium alloy occurs and may cause separation of the coating. In this case, therefore, it is necessary to use a coating solution not containing a halogen. Preferred coating solutions include an aqueous solution of nitric acid salts and a non-aqueous solution of organic metals which are able to slightly corrode the metallic substrate at the time of calcination as in the case of titanium or a titanium alloy, thereby increasing the bonding properties between the metallic substrate and the oxide layer.

The coating solution is coated on the metallic substrate by any desired method such as brush coating and soaking of the metallic substrate in the coating solution, and then calcining in an oxidizing atmosphere preferably at 300° to 800° C. for 5 to 30 minutes. When a coating sufficiently large in thickness cannot be obtained by only one coating and calcination procedure, the procedure can be repeated until the desired thickness can be obtained.

On the oxide layer thus provided on the metallic substrate is then formed a coating of calcium phosphate. The calcium phosphate as used herein mainly means apatite hydroxide and additionally includes tricalcium phosphate, calcium hydrogenphosphate and calcium dihydrogenphosphate which are considered to be by-produced at the time of calcination of apatite hydroxide, and calcium phosphate-based compounds formed from apatite hydroxide and impurity components or components of the oxide layer.

The method of forming the coating and conditions under which the method is carried out are not critical. Typical methods include a plasma spray coating method and a thermal decomposition method.

The plasma spray coating method has an advantage of being able to easily form the coating although it suffers from disadvantages in that it needs expensive apatite hydroxide and the yield is not sufficiently high. When spray coating is applied directly onto the metal, it should be carried out under severe conditions in order to obtain satisfactory bonding properties, and such severe conditions cause partial decomposition of the expensive apatite hydroxide. In the present invention, on the other hand, since the coating of calcium phosphate is formed on the oxide layer, sufficiently satisfactory bonding properties can be obtained even if spray coating is applied under such conditions as not to cause decomposition of apatite hydroxide.

It suffices that the spray coating is carried out in an atmosphere comprising argon gas and hydrogen and the electric power is about 30 kW. The particle diameter of apatite hydroxide is preferably intermediate in size, for example from about 125 to 345 mesh.

In the case of the thermal decomposition method, a nitric acid aqueous solution in which calcium phosphate, preferably apatite hydroxide is dissolved and preferably saturated is coated on the surface of the oxide layer and then calcined to form a coating layer having good bonding properties to the oxide layer on the metallic substrate. In this case, the calcination product is mainly a calcium phosphate compound comprising apatite hydroxide. The optimum calcination conditions vary with the solution, particularly the nitric acid concentration. As the nitric acid concentration is increased, the optimum temperature is increased. The optimum temperature is 350° to 500° C. at 10% nitric acid and 450° to 800° C. at 60% nitric acid. The calcination temperature is preferably in the range of 300° to 800° C. If the calcination temperature is less than 300° C., the coating of calcium phosphate is insufficiently low in strength. On the other hand, if it is more than 800° C., the metallic substrate is seriously oxidized and the separation of the oxide layer from the metallic substrate easily occurs. Although the calcination can be carried out in an oxidizing atmosphere exemplified by air, it is preferred to be carried out in an inert atmosphere exemplified by argon.

The coating layer can also be formed by coating a solution of a mixture of calcium carbonate and calcium phosphate in a suitable ratio and then calcinating in an oxidizing or inert atmosphere. In this case, it is preferred that hydrothermal treatment be applied to increase crystallinity.

In accordance with the above procedures, there can be obtained an implant material which is good in workability, is sufficiently high in mechanical strength, has increased affinity in the bone tissue and living body, and can hold stable bonding properties to the living body over a long time.

The present invention is described in greater detail with reference to the following examples although it is not intended to be limited thereto.

Unless otherwise specified, all rates, percents, etc. are by weight.

EXAMPLE 1

A 40 mm×20 mm piece was cut out of a JIS No. 1 titanium rolled sheet having a thickness of 1 mm. The surface of the piece was made coarse by applying blast treatment with a #80 steel shot, and then washed by soaking in a 25% sulfuric acid aqueous solution maintained at 90° C. for 30 minutes. This piece was used as a substrate. On this titanium substrate, a 10% hydrochloric acid solution of a mixture of tantalum chloride containing 10 g/l of tantalum and titanium chloride containing 10.4 g/l of titanium was coated and dried, which was then calcined in a muffle furnace maintained at 450° C. for 10 minutes. The above procedure was repeated to form an intermediate oxide layer of $1.0 \times 10^{-2}$ mol/m$^2$ of a titanium oxide-tantalum oxide ($TiO_2$-$Ta_2O_5$) mixed oxide (molar ratio of Ti to tantalum: 80:20). The apparent thickness of the oxide layer was about 0.3 μm.

About 3 g of apatite hydroxide power was gradually added to 10 g of a 25% aqueous nitric acid solution while fully stirring to prepare a coating solution. This coating solution was coated on the oxide layer of the titanium substrate, which was immediately placed in a stream of argon and dried at 60° C. for 20 minutes, and then calcined by heating at 500° C. for 10 minutes in the same atmosphere as above. This heat calcination procedure was further repeated twice. A white coating formed on the surface was very firmly bonded to the underlying titanium substrate, X-ray diffraction confirmed that it was apatite hydroxide having good crystallinity.

EXAMPLE 2

A 40 mm×20 mm piece was cut out of a stainless steel SUS 316L rolled sheet having a thickness of 1 mm. The surface of the piece was made coarse by applying blast treatment with a #70 corrondum grid and further washed by soaking in a 30% aqueous FeCl$_3$ solution at 25° C. for 4 minutes. This piece was used as a substrate. On this stainless steel substrate, a butanol solution of niobium ethoxide and titanium ethoxide (niobium: 5.1 g/l; titanium: 10.5 g/l) was coated and dried, which was then calcined in a muffle furnace maintained at 450° C. for 10 minutes. This procedure was repeated twice to form an intermediate oxide layer of $1.0 \times 10^{-2}$ mol/m$^2$ of a titanium oxide-niobium oxide ($TiO_2$-$Nb_2O_5$) mixed oxide (molar ratio of titanium to niobium, 80:20).

About 3 g of apatite hydroxide powder was added to 10 g of a 25% nitric acid aqueous solution to prepare a coating solution. This coating solution was coated on the oxide layer of the stainless steel substrate, dried in a stream of argon at 60° C. for 20 minutes, and further calcined by heating in the same atmosphere as above at 500° C. for 10 minutes. This heat-calcination procedure was further repeated twice. A white coating layer formed on the surface was firmly bonded to the underlying stainless steel substrate. X-ray diffraction confirmed that it was apatite hydroxide having good crystallinity.

EXAMPLE 3

On a JIS No. 1 titanium rolled sheet was formed an intermediate oxide layer of $1.0 \times 10^{-2}$ mol/m$^2$ of a mixed oxide of titanium oxide-tantalum oxide ($TiO_2$-$Ta_2O_5$) (molar ratio of titanium to tantalum, 80:20) under the same conditions as in Example 1.

On the oxide layer, apatite hydroxide granules adjusted in particle size to about 125 to 345 mesh were plasma spray-coated under conditions as shown in Table 1. A white coating layer formed on the surface was very firmly bonded to the underlying titanium substrate. X-ray diffraction analysis confirmed that it was apatite hydroxide having good crystallinity.

TABLE 1

| Flow Rate of Plasma Gas | |
|---|---|
| Ar | 30 l/min |
| H$_2$ | 6 l/min |
| Flow Rate of Carrier Gas | 6 l/min |
| Arc Voltage (DC) | 60 V |
| Arc Current (DC) | 500 A |
| Spraying Distance | 100 mm |

Some of the advantages of the present invention are described below.

(1) Since corrosion resistant titanium, titanium alloys or stainless steel are used as the metallic substrate and the metal oxide layer is formed on the surface of the metallic substrate, the composite material of the present invention, when used as an artificial bone or artificial tooth root, is harmless to the living body, is stable, is almost free of the possibility of dissolution, and further is sufficiently high in mechanical strength and is easily worked.

(2) Since the surface of the metallic substrate is covered with a calcium phosphate compound exemplified by apatite hydroxide, the composite material of the present invention exhibits sufficiently high affinity in the living body and thus can be bonded to the bone in the living body with ease and further with high strength.

(3) Since, as described above, the metal oxide layer is formed on the surface of the metallic substrate, even when the calcium phosphate particularly excellent in affinity is absorbed in the bone tissue over a long time after implantation in the living body, the oxide layer formed on the metallic substrate prevents the metallic substrate from coming into direct contact with the bone tissue and also prevents degradation of bonding properties between them as based on insufficient affinity between the bone tissue and the metallic substrate. Thus the calcium phosphate-coated composite material of the present invention can be used as an implant material without causing any change in the stability thereof for a long time.

(4) Since the metal oxide layer is formed between the calcium phosphate coating and the metallic substrate and the coating can be firmly bonded on the metal oxide layer by plasma spray coating even under relatively mild conditions, the coating layer can be formed easily and it becomes possible to employ the spray coating method which has not been employed because of decomposition of apatite hydroxide.

While the invention has been described in detail and with reference to specific embodiments thereof, it will be apparent to one skilled in the art that various changes and modifications can be made therein without departing from the spirit and scope thereof.

What is claimed is:

1. A process for producing a calcium phosphate coated-composite material which comprises coating a coating solution containing one or more metals selected from the group consisting of titanium, zirconium, hafnium, vanadium, niobium, tantalum, tin, cobalt, aluminum, chromium, molybdenum and tugsten on the surface of a metallic substrate, converting the one or more metals into a corresponding oxide by heating in a oxidizing atmosphere to form an oxide layer, and then forming a coating of calcium phosphate on the surface of the oxide layer.

2. The process as claimed in claim 1, wherein the metallic substrate is made of titanium or a titanium alloy.

3. The process as claimed in claim 1, wherein the metallic substrate is made of a corrosion resistant iron alloy and the coating solution is a solution containing neither halogen ions nor halogen compounds.

4. The process as claimed in claim 1, wherein the formation of the oxide layer by heat treatment is carried out by calcinating at a temperature not less than 300° C.

5. The process as claimed in claim 2, wherein the formation of the oxide layer by heat treatment is carried out by calcinating at a temperature not less than 300° C.

6. The process as claimed in claim 3, wherein the formation of the oxide layer by heat treatment is carried out by calcinating at a temperature not less than 300° C.

7. The process as claimed in claim 1, 2, 3, 4, 5 or 6, wherein the coating of calcium phosphate is carried out by plasma spray coating of calcium phosphate and/or apatite hydroxide power.

8. The process as claimed in claim 1, 2, 3, 4, 5 or 6, wherein the coating of calcium phosphate is carried out by coating a nitric acid aqueous solution of apatite hydroxide as a coating solution on the surface of the oxide layer, and then calcining the coating solution at a temperature not less than 300° C.

* * * * *